US005094848A

United States Patent [19]

Brixner

[11] Patent Number: 5,094,848

[45] Date of Patent: Mar. 10, 1992

[54] CLEAVABLE DIPHOSPHATE AND AMIDATED DIPHOSPHATE LINKERS

[75] Inventor: Diana I. Brixner, Lynnwood, Wash.

[73] Assignee: Neorx Corporation, Seattle, Wash.

[21] Appl. No.: 373,426

[22] Filed: Jun. 30, 1989

[51] Int. Cl.$^5$ ...................... A61K 39/44; C07K 17/10; C07K 17/06

[52] U.S. Cl. ................................ 424/85.91; 530/345; 530/405; 530/409; 530/332; 530/391.5; 530/391.9; 514/2; 514/21; 536/51; 424/9; 424/1.1

[58] Field of Search ............... 530/345, 391, 409, 405, 530/332; 536/51; 424/85.91; 514/2, 21

[56] References Cited

PUBLICATIONS

Gregoriadis (1980) Pharmac. Ther. 10:103-118.

Ghose et al. (1982) Nato. Adv. Study Inst. Ser., Ser A, vol. 47, pp. 55-82.

Blair et al. (1983) J. Immunol. Methods, 59:129-143.

Molteni (1979) in *Drug Carriers in Biology and Medicine* pp. 107-128 Academic Press.

Hong et al., Biochem. Biophys. Res. Comm., 94, (1980) 1169.

Ryu et al., Med. Chem., 25, (1982) 1322.

Hong et al., J. Med. Chem., 28, (1985) 171.

Rosowsky et al., J. Med. Chem., 25, (1982) 171.

Hong et al., J. Med. Chem., 31, (1988) 1793.

*Primary Examiner*—Jeffrey E. Russel

*Assistant Examiner*—Kay Kim

*Attorney, Agent, or Firm*—Millen, White and Zelano

[57] ABSTRACT

The specificity of a pharmaceutical agent for a given site of action is increased by covalently bonding the agent via a diphosphate or amidated diphosphate bond to a targeting moiety, preferably a polypeptide specific for the site.

27 Claims, No Drawings

CLEAVABLE DIPHOSPHATE AND AMIDATED DIPHOSPHATE LINKERS

BACKGROUND OF THE INVENTION

This invention relates to compounds containing a cleavable linker between a deliverable compound, e.g., a pharmaceutical agent, and a targeting moiety, e.g., a protein.

There are many diagnostic and therapeutic agents which suffer from non-selectivity of effect. Thus, cells not in need of a particular treatment are nevertheless exposed to the treating agent. Analogously, cells not intended to be the subject of a diagnosis, e.g., an imaging procedure such as radioimaging or MRI, are nevertheless subjected thereto, i.e., are imaged. As a result of this pervasive non-selectivity problem, much effort has been expended to enhance the selectivity of such pharmaceutical agents.

One technique often used is the binding of the non-selective pharmaceutical agent to another chemical moiety which is capable of targeting the resultant conjugate to a desired site. In most cases, the conjugate must also provide a means for cleaving the "active" agent from the targeting portion. This combination of features poses a unique biochemical problem: Not only must the conjugate provide a targeting moiety specific for a given site, but the cleavability must also be functional at that site and in such a manner that the agent retains its therapeutic or diagnostic capabilities.

In one general method, a protein such as a monoclonal antibody is attached to the pharmaceutical agent. The antibody is selected to be specific for the type of cells desired to be treated or diagnosed. The targeting portion has been attached to the pharmaceutical agent by a variety of linking groups, some of which are cleavable linkers.

Heretofore, the diphosphate (DP) group has been used as a linker between certain molecules. This group is hydrolyzed (cleaved) in situ by enzymes such as phosphodiesterase (EC 3.1.4.1), 5'-nucleotidase (EC 3.1.3.5), and acid phosphatase (EC 3.1.3.2), inter alia. Investigations have been reported using DP to form conjugates of the anti-tumor agent Ara-C (1-β-arabinofuranosylcytosine), with other active agents (steroids), and with lipophilic groups such as aliphatic chains (e.g., alkyl, alkoxyalkyl, etc.). See, e.g., Hong, C. I., Nechaev, A., West, C. R., *Biochem. Biophys. Res. Comm.*, 94, (1980) 1169; Ryu, E. K., Ross, R. J., Matsushita, T., MacCoss, M., Hong, C. I., West, C. R., *J. Med. Chem.*, 25, (1982) 1322; Hong, C. I., Kirisits, A. J., Nechaev, A., Buchheit, D. J., West, C. R., *J. Med. Chem.*, 1985) 171; Rosowsky, A., Ross, H. S., Wick, M. M., *J. Med. Chem.*, 25, (1982) 171; and Hong, C. I., S. H., Schliselfeld, L., Buchheit, D. J., Nechaev, A., Kirisits, A. J., West, C. R., *J. Med. Chem.*, 31, (1988) 1793. The conjugate was theorized to protect against enzymatic degradation of the active moiety and/or the lipophilic groups had been theorized to enhance cellular uptake of the agent by increasing permeability to cell membranes. These investigators, however, report widely varying effects on the bioavailability of the active agent, both increasing and decreasing efficacy, depending on the nature of the lipophilic moiety as well as the nature of the cleavable group, i.e., diphosphate or monophosphate.

Cleavable diphosphate linking groups have never been employed for the purpose of targeting agents to desired, e.g., in vivo, sites. Thus, for example, they have not heretofore been linked to polypeptide, e.g., proteinaceous, or other targeting groups. In part, this is due to the difficulty of synthesis and of appropriately attaching the necessary portions to each other while retaining all attributes necessary for a successful site-directing conjugate. For example, direct specific phosphorylation of a hydroxy or other nucleophilic group of an antibody is not viable, since there would be no selectivity towards, e.g., OH or $NH_2$ group. Amino or hydroxy groups, respectively, and other nucleophilic groups would also be phosphorylated. Moreover, a linker comprising such a phosphorylated group would not cleave as desired. As a result, a synthetic linker needs to be designed, which is not straightforward. For example, simple straight-chain hydroxy acids are not applicable as linking components due to spontaneous lactone formation, and glyceric acid with isopropylidene protected hydroxy groups is also inappropriate, since self-destructive deketalization is catalyzed by internal carboxylic acids.

SUMMARY OF THE INVENTION

This invention provides a method of targeting a deliverable compound such as a pharmaceutical agent to a desired site in a patient or sample comprising administering to the patient or contacting the sample with the deliverable agent bound by a cleavable diphosphate or amidated diphosphate linkage to a targeting moiety, e.g., a polypeptide, especially a protein specific for the site. This invention also relates to the conjugate of the agent linked to the targeting moiety such as a polypeptide by the diphosphate or amidated diphosphate linkage. As a result, the deliverable compound has increased specificity for a desired site. Another advantage of this invention is the high water solubility of the derivatives provided by the diphosphate and amidated diphosphate linker.

Thus, in one aspect, this invention provides a conjugate useful for targeting of an active agent to a desired site, comprising an active agent cleavably linked to a moiety effective for targeting to said site, wherein said active agent is linked by the group $—L^1_n—DP—L^2$ or $—L^1_n—DP(A)—L^2—$, wherein DP is diphosphate, DP(A) is amidated diphosphate, $L^1$ is a bridging spacer group, n is 0 or 1, and $L^2$ is a linking arm.

In a preferred aspect of the invention's chemical structure, the active pharmaceutical agent is bound to one side of a diphosphate linkage and a targeting moiety, such as a polypeptide, is bound to its other side, e.g., by a linking arm which is, e.g., an oligopeptide moiety, preferably a dipeptide.

One class of compounds useful for targeting of an active agent (in vitro or in vivo) comprises the structure:

A-bridge-targeting moiety, wherein:

A is an active agent or a portion thereof,

"targeting moiety," preferably a targeting polypeptide, is linked covalently to the bridging moiety, e.g., by a polypeptide conjugating moiety, and the bridging moiety is:

$$—L^1_n—DP—L^2—$$

wherein:

DP is phosphate

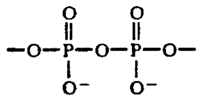

$L^1$ is an optional bridging spacer group between A and DP, n is 0 or 1, and $L^2$ is a linking group connecting DP with the targeting moiety while retaining the targeting capability of the moiety, e.g., a polypeptide; preferably $L^2$ is an oligopeptide moiety linked to DP by an O-atom of the latter.

For the alternative amidated diphosphate ("phosphoramide" or "phosphamide" or "phosphoramidate") embodiment of this invention (cleavable in situ, e.g., by phosphoramidases and also by alkaline phosphatases, etc.), DP in the formula above is replaced by DP(A) (amidated diphosphate)

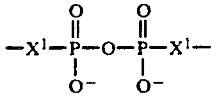

wherein one $X^1$ is O and the other is NH. Thus, one of $L^2$ and $L^1$ will be, linked to DP(A) by —NH— and the other by O—, since the N atom can reside on either the active agent side or the targeting moiety side. Of course, within the scope of this invention are also included salts of the diphosphates and amidated diphosphates, as well as other possible equivalent structures, e.g., wherein O might exist as OH.

This invention also relates to methods for preparing the targeting conjugates of this invention as well as various subunits thereof, e.g., $L^1$ —DP, $L^1$ —DP(A), DP—$L^2$, DP(A)—$L^2$, $L^1{}_n$—DP—$L^2$, $L^1{}_n$—DP-(A)—$L^2$, etc. In one especially preferred aspect, to form $L^2$, a dipeptide is formed between an optionally protected amino acid containing a hydroxy group and an optionally protected second amino acid, and then either the hydroxy group or an amino group (when —N—in DP(A) is on the targeting moiety side) is phosphorylated and the resultant phosphate or phosphoramide group is coupled to a phosphate or phosphate precursor compound to form a diphosphate bond, thus forming the DP or DP(A) linker structure.

In another aspect of this invention, the "A-bridge" portion of the mentioned structure can be contained more than once in the conjugate, e.g., by linkage to a polymeric substrate "carrier" such as, e.g., dextran or synthetic polymers. These provide a backbone having pendant groups, e.g., nucleophilic groups such as oxo, hydroxy, or amino groups to which an active agent can be linked per the methods of this invention. For example, any synthetic polypeptide that contains or is modified to contain serine amino acids can be phosphorylated and then attached to drugs per this invention. The polymeric substrate can be conventionally derivatized for conjugation to the targeting group, e.g., via a diphosphate linker or using the chemical methods discussed below, e.g., via an NHS or other active ester, e.g., of a terminal carboxylic acid, or other conventional means.

Thus, schematically, such structures include:

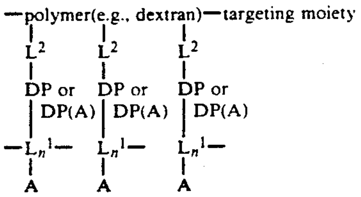

Details are analogous to known drug carrier approaches, e.g., as discussed in Molteni, L. "Drug Carriers in Biology and Medicine," pp. 107-128 Academic Press, N.Y. (1979); and Shouval, D.; Adler, R.; Wands, J. R.; Hurwitz, E; Isselbacher, K. J.; Sela, M. Proc. Natl. Acad. Sci. 85, 8276-8280, (1988). Besides increased active agent loading, other advantages of this aspect of the invention include increased water solubility when the carrier contains polar groups.

In one aspect, this invention overcomes the above-noted difficulties in making DP conjugates (and, analogously, difficulties in making DP(A) conjugates) by utilizing the $L^2$ linking approach. The $L^2$ structure in the conjugates of this invention is generally formed by reaction of an $L^2$ "precursor" with DP (DP(A)) or DP (DP(A)) precursors and with the targeting polypeptide or a conjugating group precursor. An $L^2$ precursor provides components of the two necessary connecting moieties, e.g., a hydroxy or amino group (optionally in protected form) which is typically reacted to form an intermediate moiety (generally MP or amidated MP(≡MP(A)) eventually providing the diphosphate or amidated diphosphate linkage (or to form DP or DP(A) itself, where applicable); and any one of the many known conjugation groups for linking to proteins. In addition, $L^2$ must have an appropriate length to ensure the cleavability of the DP or DP(A) ( group in situ and the appropriate placement of the group A—$L^1{}_n$—(MP) or —(MP(A)) at the site of release; e.g., if the linking arm $L^2$ is too long, the active moiety may be less appropriately positioned for its diagnostic or therapeutic effect. For example, $L^2$ desirably is of a length that permits ready access of the adjacent amidated diphosphate or diphosphate group to the enzyme that effects its cleavage.

The structure of $L^2$ is especially important in certain conjugates, such as those comprising relatively large molecules, such as large drugs, as the active agent. In such cases, binding of the enzyme to the DP or DP(A) group may be reduced by steric hindrance if $L^2$ is enzyme may be reduced when an $L^2$ oligopeptide is too , long, due to the secondary structure (e.g., folding, disulfide bond formation, etc.) in the oligopeptide. The desired water solubility of the oligopeptide also may be reduced if it is too long. These principles were demonstrated by Trouet et al. where daunorubicin covalently linked to succinylated albumin was only released extensively from conjugates prepared with a tri- or tetrapeptide spacer arm. See Trouet, A., Mosquelier, M. *Proc. Natl. Acad. Sci. USA,* 79, 1982, 626-629. For this invention, arms can typically have up to about 30 atoms in the $L^2$ linker backbone, e.g., 2-30 atoms, e.g., for oligopeptides, up to about 10-mers. However, these quantitative ranges are meant to be guidelines only and not limitative in any way. As long as an $L^2$ arm performs the functions described herein, it is part of this invention.

In a most preferred aspect of this invention, $L^2$,will be an oligopeptide, preferably a dipeptide, but more generally a peptide having from 2-10 amino acid units, as described above. For DP linkers, one of the amino acid units, preferably one of the terminal units, will preferably have a hydroxy group, e.g., serine or threonine, but any other hydroxy amino acid will also be employable. The hydroxy or amino groups can be phosphorylated using any of the well-known conventional techniques, the hydroxy or amino groups being reversibly blocked or activated as necessary. Of course, other groups on the peptide linkage will similarly be blocked where necessary using conventional methods.

Phosphorylation may be accomplished, for example, by conventional reaction with beta-cyanoethylphosphate. See, e.g., Tener, G. M., *J. Am. Chem. Soc.*, 83, (1961) 159; Brownfield, R. B., Shultz, W., *Steroids*, 2, (1963) 597. In another technique, dibenzylphosphorylchloridate can be used as the phosphorylating reagent. See Kenner, G. W.; Fortsch. *Chemie Org. Naturstoffe*, 8, (1951) 96. Also utilizable is phosphoric acid itself. See U.S. Pat. No. 3,068,223; Hong et al. (1985), supra. Kenner also discloses a wide variety of other phosphorylating reagents which can be utilized. See also Franke, A., Scheit, K. H., Eckstein, F., *Chem. Ber.*, 101, (1968), 2998-3001; Slotin, L. A., *Synthesis*, 1977, 11, 737; and Amarnath, V., Broom, A. D., *Chem. Rev.*, 1977, 77, 183. The choice of a particular agent, of course, will be made in consideration of conventional factors, including possible interfering side groups on the linking arm, the availability of suitable protecting agents, reactivity of the compounds involved, yields, etc. In preliminary experiments, the $\beta$-cyanoethyl phosphate method appears especially attractive. At most, a few routine orientation experiments might be necessary to determine an optimum phosphorylating agent in a given case.

Phosphorylation of the hydroxy or amino group on the linker arm can be effected after preparation of the complete, optionally protected linker arm, with or without the conjugating moiety and/or the protein. Alternatively, the phosphorylation can be carried out as a first step or at any stage during the preparation of the oligopeptide linker arm.

In addition to the "natural" amino acids, any other modified natural or synthetic amino acid can be employed in a synthetic scheme for preparation of the linker arm $L^2$ (as well as the linker arm $L^1$ discussed below). These include, for example, gamma-aminobutyric acid (GABA), 2-aminoisobutyric acid, mono- or di-$C_{1-6}$-alkylglycine, other alkylated amino acids, amino acids based on straight or branched chain alkyl groups of 2-10 C atoms having an amino group on one terminus and a carboxy group on another terminus and optionally substituted by $C_{1-6}$-alkyl, hydroxy, amino, mercapto, oxo, etc. The alkyl chains can also be interrupted by O, N, or S atoms. Suitable substituents also include $C_{6-10}$-aryl groups, such as phenyl or naphthyl, and $C_{6-10}$-ar-$C_{1-4}$-alkyl groups, e.g., benzyl.

While oligopeptides are preferred as linker arms $L^2$, any chemical moiety, all of which are included or contemplated equivalents of the $L^2$ element of the invention, will suffice in accordance with this invention as long as it provides the functions defined herein for $L^2$ (e.g., retention of the cleavability of DP or DP(A) and the specificity of the targeting, e.g., polypeptide moiety). $L^2$ arms will typically provide an oxygen or nitrogen atom for linking to the phosphate, typically via an OH or $NH_2$ group as precursor, and a conjugatable group for linking to the targeting, e.g., protein moiety, these two groups normally being separated by a chain of 2-30 atoms, as mentioned above, typically C atoms but also N, O or S or other atoms. A few non-limiting examples of groups from which the linker arm $L^2$ can be derived include any chemically compatible group containing, e.g., carboxyl on one end for conjugation and, e.g., hydroxy or amino on the other for phosphorylation. More generally, non-limiting examples include structures X—Y—Z, wherein one of X and Z is a group, e.g., OH or NHz as described above, which results in a bond to DP or DP(A) in the final structure, and the other is a group which can be used to conjugate, e.g., to a targeting polypeptide or to form such a conjugatable group, (e.g., active esters, halo, $NH_2$, OH, COOH, etc.). Y is an organic bridging portion, e.g., aliphatic and/or aryl and/or alicyclic and/or heterocyclic, preferably aliphatic, of an appropriate length as described above, optionally interrupted by one or more of oxygen, nitrogen, sulfur, amido, —COO, —OCO—, etc.

Groups described herein for $L^1$ will also be suitable in general for use as $L^2$ arms where they meet the foregoing criteria.

The most simple preferred $L^1$ linking arm per this invention is the dipeptide -Ser-GABA-, the synthesis of which is described in Example 1 below. "Ser" represents an acetylated derivative of the amino acid serine and "GABA" is gamma-aminobutyric acid. Preferably, $L^2$ also comprises a conjugation group that will react with a targeting polypeptide.

The linking arm $L^1$ is optional (i.e., n can be 0 or 1). Whether the linking arm $L^1$ is used will depend on the structure of A, the structure of the active version of A, if different, and the chemical and therapeutic or diagnostic nature and requirements of A. For example, when A is an active agent itself containing a phosphate or phosphoramide group, there will usually be no need for the linking arm $L^1$. If, on the other hand, $L^1$ is a ligand, e.g., useful for chelating a radioactive element, then a linking arm $L^1$ may be useful, e.g., to facilitate chemical coupling of A to the DP or DP(A) linkage and/or enzymatic cleavage of the latter.

The precise nature of $L^1$ is not critical in accordance with this invention. Essentially any bridging group can be utilized which is derived from an $L^1$ precursor (used to form $L^1$ in the preparation of the conjugates of the invention) which provides means for effecting attachment to the DP or DP(A) moiety and means for attachment to active agent A. Very often, amino acid or peptide linker arms will be utilizable. In this case, the various embodiments discussed with respect to $L^2$ will be suitable. Other linking groups can also be employed of the most diverse nature, e.g., as mentioned above for $L^2$.

The $L^1$ linker generally will be an organic group which is aliphatic, alicyclic, aromatic, or heterocyclic, preferably aliphatic. $L^1$ typically comprises from one to about ten carbon atoms, preferably from one to six carbon atoms in the form of a chain that may have heteroatoms (e.g., nitrogen, oxygen, and/or sulfur atoms) substituted within or on the carbon chain. The $L^1$ precursor may also comprise a hydroxy or amino group (or protected hydroxy or amino group) which may be phosphorylated or through which $L^1$ may be bonded to a phosphate or phosphoramide group of the DP or DP(A) moiety. An amino acid comprising a hydroxy group (e.g., serine or threonine) or a derivative thereof may be included in the $L^1$ linker precursor, for example. Alternatively, the $L^1$ precursor may comprise hydroxy amines, hydroxy acids, etc.

As is clear from the following, the individual components of the compounds of the present invention (e.g., the agent, $L^1$, DP, DP(A), $L^2$ and the targeting, e.g., polypeptide portion) do not necessarily have to be synthesized separately and subsequently joined together. Instead, an agent such as a chelating compound may be synthesized to include all or part of a desired $L^2$ linker, for example. In addition, commercially available phosphorylated compounds may be employed, which comprise all or a portion of $L^1$ or $L^2$, as well as one of the phosphate or phosphamide groups of the final conjugates of the invention. Several examples are given below.

Some exemplary linkages incorporating structure of $L^1$ and optionally also a portion of DP or DP(A), include aliphatic chains, extended carbonates, hemiesters, sulfates, organic phosphate, pyrophosphates, carbamates, phosphamides, glucuronides, etc. See, e.g., Sinkula, A. A., Yalkowsky, S. H. *J. Pharm. Sci.*, 64, 181-210 (1975). A particularly useful linking agent is the very simple compound ethanolamine or, more preferably, ethanolamine phosphate which is commercially available (Sigma).

The diphosphate linkage can be prepared conventionally by linking phosphate groups on two compounds, e.g., (a) a phosphate group on $L^2$ or a portion thereof, and (b) a phosphate group on A or a portion of A or on all or part of $L^1$, all such compounds being suitably blocked where necessary for reaction. The diphosphate linkage can be conventionally effected using the morpholidate technique of Moffatt et al. See Moffatt, J. G., Khorana, H. G., *J. Am. Chem. Soc.*, 83, (1961) 649], Wherein a morpholidate of a phosphate group is linked to a free phosphate group. The morpholidate group can be prepared from the $PO_4$ group of either side of the diphosphate linkage for coupling to the other side thereof. Other techniques for preparing the diphosphate bond can also be used, e.g., reaction of a phosphate with diphenyl phosphochloridate (Michelson, A. M., *Biochem. Biophys. Acta*, 91, 1, (1964); Furusawa, K., Sekine, M., Hata, T., *J. Chem. Soc.*, Perkin Trans. 1, 1711 (1976). The DP(A) structure can be formed fully analogously where one of the mentioned phosphate groups is replaced by a phosphamide group.

Throughout all of the foregoing, the amino acids and other components often can exist in several enantiomeric forms. All such forms and mixtures thereof are also included. Typically, the L-forms are preferred.

Throughout the various synthetic steps, various chemical groups on the starting materials and intermediates, typically hydroxy or amino groups, will be conventionally protected by well known methods for subsequent liberation of the desired end products also by conventional methods, e.g., solvolysis, particularly hydrolysis, or by hydrogenolysis. These starting materials and/or intermediates will correspond to the conjugate of this invention or portions thereof; however, instead of one or more free amino and/or hydroxyl groups, for example, there will be a corresponding protected amino and/or hydroxyl group(s). The protected amino and/or hydroxyl groups can be the same or different; in the latter case, they often can be split off selectively.

The term "amino protective group" is generally known and relates to groups which are suitable for protecting (blocking) an amino group against chemical reactions, but which can be removed readily after the desired chemical reaction has been carried out at another point on the molecule. Typical representatives of groups of this kind are, in particular, unsubstituted or substituted acyl, aryl [for example, 2,4-dinitrophenyl (DNP)], aralkoxymethyl (for example benzyloxymethyl (BOM) or aralkyl (for example benzyl, 4-nitrobenzyl or triphenylmethyl) groups. Where the amino protective groups are to be removed after the desired reaction (or reaction sequence), their nature and size will not be critical; groups having 1-20, in particular 1-8, C atoms are, however, preferred. In the context of the present invention, the term "acyl group" is to be understood in the widest sense. It embraces acyl groups derived from aliphatic, araliphatic, aromatic or heterocyclic carboxylic acids or sulfonic acids and also, in particular, alkoxycarbonyl, aryloxycarbonyl and, above all, aralkoxycarbonyl groups. Examples of acyl groups of this type are alkanoyl, such as acetyl, propionyl or butyryl; aralkanoyl, such as phenylacetyl; aroyl, such as benzoyl or toluyl; aryloxyalkanoyl, such as phenoxyacetyl (POA); alkoxycarbonyl, such as methoxycarbonyl, ethoxycarbonyl (ETOC), 2,2,2-trichloro-ethoxycarbonyl, t-butoxycarbonyl (BOC) or 2-iodoethoxycarbonyl; and aralkyloxycarbonyl, such as CBZ (benzyloxycarbonyl "carbobenzoxy"), 4-methoxybenzyloxycarbonyl or 9-fluorenylmethoxycarbonyl (FMOC). Preferred amino protective groups are DNP and BOM, and also CBZ, FMOC, benzyl and acetyl.

The term "hydroxyl protective group" is also generally known and relates to groups which are suitable for protecting a hydroxyl group against chemical reactions, but which can be removed readily after the desired chemical reaction has been carried out at another point in the molecule. Typical representatives of such groups are the unsubstituted or substituted aryl, aralkyl or acyl groups mentioned above, and also alkyl groups. The nature and size of the hydroxyl protective groups is not critical where they are removed again after the desired chemical reaction or reaction sequence; groups having 1-20, in particular 1-10, C atoms are preferred. Examples of hydroxyl protective groups are, inter alia: benzyl, p-nitrobenzoyl, p-toluenesulfonyl and acetyl, benzyl and acetyl being particularly preferred.

Activated and protected derivatives of the compounds, starting compounds and intermediates of the invention to be used in the syntheses can be prepared by customary methods of amino acid and peptide synthesis, such as are described, for example, in standard works, e.g., Greene, T. W. "Protective Groups in Organic Synthesis". John Wiley & Sons, 1981, New York, NY, and also, for example, by the Merrifield solid phase method.

Liberation of compounds from their protected precursors can be effected—depending on the protective group used—with, for example, strong acids, preferably trifluoroacetic acid (TFA) or perchloric acid, but also other strong inorganic acids, such as hydrochloric acid or sulfuric acid, strong organic carboxylic acids, such as trichloroacetic acid, or sulfonic acids, such as benzenesulfonic or p-toluenesulfonic acid. The presence of an additional inert solvent is possible, but not always necessary. Suitable inert solvents are preferably organic solvents, for example carboxylic acids, such as acetic acid, ethers, such as tetrahydrofuran or dioxane, amides, such as dimethylformamide (DMF), halogenated hydrocarbons, such as methylene chloride, and also alcohols, such as methanol, ethanol or isopropanol, and also water. Mixtures of the above-mentioned solvents are also suitable. Trifluoroacetic acid is preferably used in excess without the addition of a further solvent; perchloric acid is preferably used in the form of a mixture of acetic acid and 70% perchloric acid in a 9:1 ratio. The reaction temperatures for the cleavage are preferably between about 0° and about 50°; the reaction is preferably carried out between 15 and 30 (room temperature).

The BOC group can be split off, for example, preferably by means of 40% trifluoroacetic acid in methylene chloride or by means of about 3 N to 5 N HCl in dioxane at 15°-30°, while the FMOC group can be split off by means of an approximately 5 to 20% solution of dimethylamine, diethylamine or piperidine in DMF at 15°-30°. Splitting off the DNP group is possible, for example, also by means of an approximately 3 to 10% solution of 2-mercaptoethanol in DMF/water at 15-30°.

Protective groups which can be removed by hydrogenolysis (for example BOM, CBZ or benzyl) can be split off, for example, by treatment with hydrogen in the presence of a catalyst (for example, a noble metal catalyst such as palladium, preferably on a support such as charcoal). Suitable solvents for this reaction are those indicated above, in particular, for example, alcohols, such as methanol or ethanol, or amides, such as dimethylformamide (DMF). As a rule, the hydrogenolysis is carried out at temperatures between about 0° and 100° and pressures between about 1 and 200 bar, preferably at 20°-30° and 1-10 bar. Hydrogenolysis of the CBZ group can be effected readily, for example, over 5 to 10% Pd/C in methanol at 20°-30°.

The formation of the peptide bond(s) can be carried out by customary methods of peptide synthesis, such as are described, for example, in Houben-Weyl, *Methods of Organic Chemistry,* Georg-Thieme-Verlag, Volume 15/II, pages 1 to 806 (1974); Bodanszky, A., Bodanszky, M., "The Practice of Peptide Synthesis" Springer-Verlag, 1984, New York, N.Y. The reactions can preferably be carried out in the presence of a dehydrating agent, for example a carbodiimide, such as DCCI (dicyclohexyl- carbodiimide), EDCI (N-ethyl-N'-(3-dimethylaminopropyl)-carbodiimide hydrochloride), or dimethylaminopropylethylcarbodiimide, (See, e.g., Williams et al., *Chem. Rev.,* 1981, 589-636), ; and also propanephosphonic anhydride, diphenylphosphoryl azide or 2-ethoxy-N-ethoxycarbonyl-1,2-dihydroquinoline, in an inert solvent, for example a halogenated hydrocarbon, such as methylene chloride, an ether, such as tetrahydrofuran or dioxane, an amide, such as DMF or dimethylacetamide, or a nitrile, such as acetonitrile, at temperatures between about −10° and 40°, preferably between 0° and 30°. Peptide amides can also be made using 4methylbenzhydrylamine-derivatized, cross-linked polystyrene-1% divinylbenzene resin and peptide acids made using PAM (phenylacetamidomethyl) resin (Stewart et al., "Solid Phase Peptide Synthesis," Pierce Chemical Company, Rockford, Ill., 1984). The synthesis can be accomplished either using a commercially available synthesizer, such as the Applied Biosystems 430A, or manually using the procedure of Merrifield et al., *Biochemistry* 21:5020-31, 1982; or Houghten, PNAS82:5131-35, 1985. The side chain protecting groups are removable using the Tam-Merrifield low-high HF procedure (Tam et al, *J. Am. Chem. Soc.* 105:6442-55, 1983). Peptides can be extracted with 20% acetic acid, lyophilized, and purified by reversed-phase PHLC on a Vydac C-4 Analytical Column using a linear gradient or 100% water to 100% acetonitrile-0.1% trifluoroacetic acid in 50 minutes. Peptides can be analyzed using PTC-amino acid analysis (Heinrikson et al., *Anal. Biochem.* 136:65-74, 1984). After gas-phase hydrolysis (Meltzer et al., *Anal. Biochem.* 160: 356-61, 1987), for example, sequences can be confirmed using the Edman degradation or fast atom bombardment mass spectroscopy.

The starting materials needed for the most part will be known. Insofar as they are not known, they can be prepared by known methods from known starting materials, for example, by the above-mentioned methods of peptide synthesis and of formation and/or splitting of protective groups.

The term "targeting polypeptide" refers to any polypeptide molecule from a dipeptide up to and including any protein or protein-containing compound or entity (e.g., glycoproteins) that binds to a desired target site. The basic requirement is that the polypeptide increase the specificity of the agent A toward a desired site, preferably in vivo, e.g., in a mammal, including humans, but also in vitro in a given sample, e.g., a mammalian fluid or tissue sample. Thus, the targeting polypeptides can include proteins having certain biological activities rendering them specific for desired sites. Protein fragments having such activity will thus also be useful as will any polypeptide which binds to an antigenic determinant on a target site such as tumor cells.

Suitable targeting polypeptides include but are not limited to receptors, hormones, lymphokines, growth factors, substrates, etc., particularly compounds binding to surface membrane receptors, where the complex may remain bound to the surface or become endocytosed. Among receptors are included surface membrane receptors, antibodies, enzymes, naturally occurring receptors, lectins, and the like. Of particular interest are immunoglobulins or their equivalents, including Fab, $F(ab')_2$ or $F_v$ fragments of antibodies.

The proteins and polypeptides may be modified as long as the biological activity necessary for the targeting of the intended diagnostic or therapeutic application is retained. For example, a modified antibody or fragment thereof may be used as long as binding to the desired antigen still occurs. Modified proteins may be produced using such techniques as genetic engineering or protein engineering.

The targeting compound binds to a desired target diagnostic or therapeutic agent to the target site. An example of a target site is a cancer site. Many antigens associated with various types of cancer cells have been identified, and monoclonal antibodies specific for a number of these cancer cell-associated antigens also are known. Such antibodies are examples of the many polypeptides suitable for use as targeting polypeptides. Among the monoclonal antibodies that bind to cancer cells are anti-TAC, or other interleukin-2 receptor antibodies; 9.2.27 and NR-ML-05 to the 250 kilodalton human melanomaassociated proteoglycan; NR—Lu-10 to 37-40 kilodalton pancarcinoma glycoprotein; and $OVB_3$ to an as yet unidentified tumor-associated antigen. As mentioned, immunospecific fragments are also included, e.g., NR—Lu-10 Fab showing specificity for breast tumors.

Any conventional means for conjugating chemical moieties to a polypeptide, typically a protein, can be employed to bond $L^2$ thereto. Any of the compatible techniques mentioned in the many publications dealing with this subject can be employed, including Vitetta, E. S., K. A., Miyama-Inaba, M., Cushley, W., and Uhr, J. W. (1983) Science (Washington, D.C.) 219, 644-650;

Yoshitake, S., Yamada, Y., Ishikawa, E., and Masseyneff, R. *Eur. J. Biochem.*, 101, (1979) 395-399; Youle, R., and Neville, D. M., Jr., *Proc. Natl. Acad. Sci. U.S.A.*. 77, (1980), 5483-5486.

For example, proteins, and polypeptides in general, contain a variety of functional groups, e.g., carboxylic acid (COOH) or free amine (—NHz) groups, which are conjugation moieties available for reaction with a suitable functional group on $L^2$. For example, an active ester on $L^2$ can react with free amine groups on lysine residues of proteins or other polypeptides to form amide bonds. Alternatively, the polypeptide may be derivatized to expose or attach additional reactive functional groups. The derivatization may involve attachment of any of a number of linker molecules such as those available from Pierce Chemical Company, Rockford, Ill. (See the Pierce 1986-87 General Catalog, pages 313-354). Alternatively, the derivatization may involve chemical treatment of the polypeptide (which may be an antibody, for example). Procedures for generation of free sulfhydryl groups on antibodies or antibody fragments also are known. See U.S. Pat. No. 4,659,839. Maleimide conjugation groups on $L^2$ are reactive with the sulfhydryl (thiol) groups.

Alternatively, when the targeting compound contains a carbohydrate, derivatization may involve chemical treatment of the carbohydrate, e.g., glycol cleavage of the sugar moiety of a glycoprotein antibody with periodate to generate free aldehyde groups. The free aldehyde groups on the antibody may be reacted with free amine or hydrazine conjugation groups on $L^2$ to bind $L^2$ to the antibody. See U.S. Pat. No. 4,671,958.

Among the preferred conjugation groups for reaction with polypeptide targeting compounds are active esters. The esters which may be utilized as conjugation groups on $L^2$ include those esters which provide a covalent amide linkage with a polypeptide in an aqueous medium. One or another of the active esters may be preferred, depending upon the particular A moiety, the polypeptide, and the conditions for conjugation, as is understood in the art of peptide chemistry. Common esters which find use are o- and p- nitrophenyl, 2-chloro-4-nitrophenyl, cyanomethyl, 2-mercaptopyridyl, hydroxy- benztriazole, N-hydroxy succinimidyl, trichlorophenyl, tetrafluorophenyl, thiophenyl, tetrafluorothiophenyl, o-nitro-p-sulfophenyl, N-hydroxy phthalimide and the like. For the most part, the esters will be formed from the reaction of the carboxylate with an activated phenol or a cyclic compound based on hydroxylamine. As other hydroxylic compounds become available, these also will find use in this invention. Imidate esters, such as methyl imidate, can be used to give amidine linkages.

This application is discussed primarily in terms of targeting polypeptides; however, equivalent targeting moieties are also part of the invention. The disclosures above and below relating to the targeting polypeptides apply analogously to the equivalent targeting moieties, especially the important aspects relating to appropriate techniques of linking the DP or DP(A) bond between A and the targeting portion. In another contemplated equivalent, a monophosphate linker, also cleavable enzymatically, is used in place of DP.

The active agent A can be a diagnostically or therapeutically useful chemical moiety.

In one particularly preferred class of site-selective compounds, A will be a radionuclide metal chelate, e.g., those disclosed in EP 188,,256 or U.S. patent application Ser. Nos. 07/076,277, now abandoned; 07/065,017, copending; 07/172,004, now U.S. Pat No. 4,965,392; or 07/201,134, now U.S. Pat. No. 4,988,496.

In one preferred class of such radionuclide chelates, the chelating compounds have the following formula:

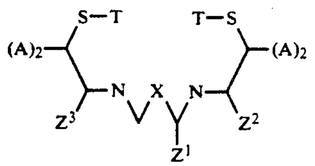

wherein:

one of $Z^1$, $Z^2$, $Z^3$ or $Z^4$ is a spacer terminating in a conjugation group, and the others are =O or $H_2$;

T is a sulfur protecting group, e.g., an acyl or acylthio radical of from 2 to 10, usually 2-8 carbon atoms, either a hydrocarbyl acyl or substituted methyl, an organic sulfhydryl radical of from 1 to 10 carbon atoms, either substituted or unsubstituted hydrocarbyl, a heterocycle, particularly a chalcogen (0, S) heterocycle, an acylamidomethylene, where the acyl group is as defined above, hydrogen, sulfonato, or an alkali metal ion;

substituents include nitro, cyano, inert halo (aryl or polyhalo), carbonyl (carboxylic acid, amide, and ester), and the like;

A's are the same or different and are hydrogen or lower alkyl of from 1 to 6 carbon atoms, usually of from 1 to 3 carbon atoms, particularly methyl and usually hydrogen; and X is a bond, methylene or $CHZ^4$.

The spacer portion of $Z^1$, $Z^2$, $Z^3$, or $Z^4$ generally will comprise an organic group which is aliphatic, alicyclic, aromatic, or heterocyclic, preferably aliphatic. The spacer typically comprises from one to about ten carbon atoms, preferably from one to six carbon atoms in the form of a chain that may have heteroatoms (e.g., nitrogen, oxygen, and/or sulfur atoms) substituted within conjugation group which is a chemically reactive group that will react with $L^1$ (or a portion thereof), or which may be phosphorylated (e.g., an optionally protected hydroxy group) to form part of the diphosphate. The conjugation group will be chosen in view of the particular conjugate to be prepared.

Thorough descriptions of such chelating moieties are contained in EP 188,256 and U.S. patent application Ser. No. 07/065,017.

A variety of metals may be employed as the radionuclide. For example, such metals include copper (e.g., $^{67}Cu$ and $^{64}Cu$); technetium (e.g., $^{99m}Tc$); rhenium (e.g., $^{186}Re$ and $^{188}Re$); lead (e.g., $^{212}Pb$); bismuth (e.g., $^{212}Bi$); and palladium (e.g., $^{109}Pd$). Methods for preparing these isotopes are known. Molybdenum/ technetium generators for producing $^{99m}Tc$ are commercially available. Procedures for producing $^{186}Re$ include the procedures described by Deutsch et al, (*Nucl. Med. Biol.*, Vol. 13:4:465-477, 1986) and Vanderheyden et al. (*Inorganic Chemistry*. Vol. 24:1666-1673, 19S5), and methods for production of $^{188}Re$ have been described by Blachot et al. (*Intl. J. of Applied Radiation and Isotopes*, Vol. 20:467-470, 1969) and by Klofutar et al. (*J. of Radioanalytical Chem.*, Vol. 5:3-10, 1970). Production of $^{109}Pd$ is described in Fawwaz et al, *J. Nucl. Med.* (1984), 25:796. Production of $^{212}Pb$ and $^{212}Bi$ is described in Gansow et al., *Amer. Chem. Soc. Symp. Ser.* (1984), 241:215-217, and Kozah et al., *Proc. Nat'l. Acad. Sci.* USA (January 1986) 83:474-478.

Radiolabelling of the compounds of this invention can be effected conventionally. For example, in a preferred embodiment of the invention discussed above, the sulfur-protecting groups T, when taken together with the two sulfur atoms to be protected, represent a thioacetal and, when taken separately, represent hemithioacetals. When such sulfur-protecting groups are used, radiolabelling of the chelating compound with technetium or rhenium may be accomplished efficiently under conditions of temperature and pH which leave base labile groups (e.g., isothiocyanates, maleimides, or ester groups) on the chelating compound intact. Such chemically reactive functional groups may be present for reaction with DP, $L^1$, or a portion thereof, as described above. The radiolabelling step may be accomplished in an exchange reaction under acidic pH conditions. When other types of protecting groups are employed, the radiolabelling step generally is conducted at a basic pH and/or relatively high temperatures. Such conditions may destroy base labile groups. In addition, the reaction mechanisms may be other than an exchange reaction in other radiolabelling procedures.

The use of thioacetal or hemithioacetal S-protecting groups has the advantage of simplifying the preparation of the radiolabelled chelate compounds and the radiolabelled polypeptides prepared therefrom. For example, a separate step for removal of the sulfur-protecting groups is not necessary. The protecting groups are displaced from the compound during the radiolabelling in what is believed to be metal-assisted acid cleavage; i.e., the protective groups are displaced in the presence of the metal radioisotope at an acidic pH, and the radioisotope is bound by the chelating compound. In general, the hemithioacetal protective groups are somewhat more acid labile in the radiolabelling reaction than the thioacetal protective groups and, therefore, are generally preferred.

In addition, base-sensitive functional groups on the chelating compound survive the radiolabelling step intact. This is especially advantageous when ester groups are present. When radiolabelling is conducted at basic pH (especially at a pH above about 9 or 10), such ester groups are substantially hydrolyzed and must be generated (or regenerated) after the radiolabelling step. Generation of the ester group generally involves a multi-step procedure (e.g., by using a carbodiimide and a hydroxylic compound, as described in the prior art mentioned above). These extra steps, and the need to remove carbodiimide and phenolic compounds (which may damage any protein subsequently added) from the reaction mixture, are avoided when thioacetal and hemithioacetal protecting groups are used. Chelating compounds comprising esters thus are ready for conjugation, e.g., to $L^1$ or a portion thereof, immediately after radiolabelling without any esterification steps.

A preferred radionuclide metal chelate is represented by the following formula:

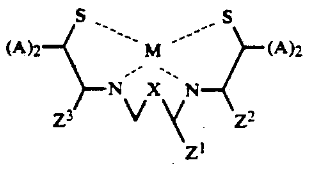

wherein M represents a radionuclide metal (which may be in the form of an oxide) and the other symbols are as described above. The dotted lines represent bonds between the radionuclide metal and the "donor atoms", which are two nitrogen and two sulfur atoms, and this chelate is therefore known as an "$N_2S_2$" chelate.

Other radionuclide metal chelates useful as the active agent component include those having a total of at least four donor atoms selected from nitrogen and sulfur atoms. During chelation, bonds form between the donor atoms and the radionuclide metal. Such chelates include, but are not limited to, the $N_3S$ chelates described in U.S. patent application Ser. No. 07/172,004 and the $N_2S_3$ and $N_2S_4$ chelates described in U.S. patent application Ser. No. 07/201,134.

Additional radiolabeled molecules useful as the active agent include molecules that bind radiohalogens at the meta or para position on a phenyl ring, as described in European Patent Application Publication No. 203,764. These compounds may be represented by the following formula:

$*H—Ar—R$ wherein

*X is a radioisotope of iodine, bromine, fluorine, or astatine;

Ar is an aromatic or heteroaromatic ring;

R is a chemical bond or a substituent containing 1 to 12 straight-chain carbon atoms that does not activate Ar toward electrophilic substitution on the order produced by hydroxy or amino substitution of the ring, wherein said bond or said substituent has attached thereto a functional group suitable for conjugation. Examples of such compounds include certain *I-paraiodophenyl compounds (in which *I represents a radioisotope of iodine) which may be prepared using the procedures described in EP 203,764, which generally involve substituting the organo-metallic group $Sn(n-Bu)_3$ or $SnMe_3$ on a haloaromatic compound. A radioisotope of a halogen then is substituted for the organometallic group by halide-metalization. Examples of radiohalogenated molecules that may be prepared using such a procedure are represented by the following formulas:

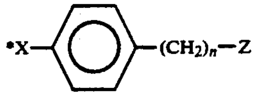

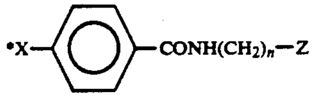

wherein n represents an integer from 0 to 3, Z represents a conjugation group, and *X represents a radioisotope of a halogen.

Other radionuclide binding molecules which may be used include the vinyl group containing compounds described in U.S. patent application Ser. No. 07/171,731, now U.S. Pat. No. 4,876,081.

Radiohalogens include any radioisotope of: iodine, particularly I-123, I-125, and I-131; bromine, particularly Br-75, Br-76, and Br-77; fluorine, particularly F-18; and astatine, particularly At-211. Preferred halogens *X for diagnostic imaging purposes include I-131 and most preferably I-123 for imaging with gamma cameras; and for position tomographic imaging: F-18, Br-75, and Br-76. For clinical radio-therapy, preferred radiohalogens *X include I-131, Br-77, and At-211.

In addition to the above-described radiolabeled molecules, any of a number of known radionuclide metal chelates or other radiolabeled molecules may be attached to a targeting polypeptide through a diphosphate-or amidated diphosphate-containing bridging moiety, in accordance with the present invention. The resultant radiolabeled targeting polypeptide can be used for diagnostic or therapeutic applications, or both (depending on the choice of radionuclide), analogously to other methods for applying radionuclide-containing compounds for these purposes. See, e.g., EP 188,256 or any of the above-cited co-pending U.S. patent applications; Kozak et al., TIBTEC, October, 1986, 262; *Radiotracers for Medical Applications,* CRC Press, Boca Raton, Fla.; and, for positron emission tomography, Heiss et al., *Positron Emission Tomography of Brain,* Springer Verlag, 1983, e.g., using $^{43}Sc$, $^{44}Sc$, $^{52}Fe$, $^{55}Co$, $^{68}Ga$, etc. The results will be enhanced in view of the enhanced site selectivity provided by this invention. The results will also be enhanced by retention of phosphate group on the ligand-containing cleavage product as long as the corresponding increase in water solubility is desirable. For example, where gut uptake of a metabolite causes imaging interference or undesirable localization of a therapeutic agent in the patient's intestines, it will be desirable to facilitate renal excretion, e.g., of a radionuclide ligand by increasing water solubility whereby clearance from the kidney and liver would be more readily effected.

A can also represent other diagnostic agents such as chelated paramagnetic metals. The resultant compounds can be useful as image enhancers for magnetic resonance imaging. See, e.g., U.S. Pat. No. 4,647,447.

Similarly, A can represent a therapeutic moiety other than a radionuclide. Especially preferred will be pharmacologically effective agents which contain a phosphate group or which are metabolized to contain a phosphate group, e.g., antitumor, antiviral or other agents. In the latter case, this invention is especially useful, since it eliminates one metabolic step. The same considerations also apply to phosphamide groups. For example, any therapeutic moiety, e.g., a cytotoxic drug, containing an amine group can be employed via the phosphoramide technology, i.e., via phosphorylation of the amine, followed by reaction with a morpholinophosphate linker. Cleavage of the phosphoramide by intracellular phosphoramidases followed by cleavage of the diphosphate releases the free amine-containing drug.

Another class of drugs to which this invention will be applicable is that wherein the existence of a phosphate (phosphamide) moiety is known not to be fatal to therapeutic activity or perhaps can even enhance it, e.g., by increasing water solubility as discussed above.

For example, in a preferred embodiment of this invention, A will represent the antitumor agent Ara-C. It is well known that Ara-C is metabolically converted by cytidine kinase to Ara-CMP and then eventually to the triphosphate.

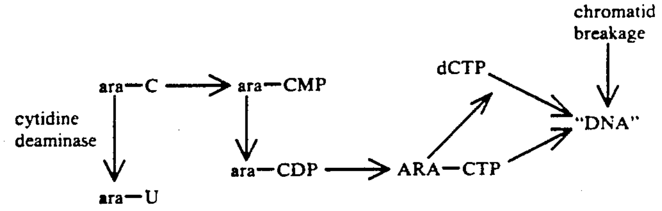

When Ara-C is linked to a targeting polypeptide via the diphosphate bond of this invention, the need for metabolic monophosphorylation is eliminated. This is a major advantage, especially since the existence of the monophosphate group eliminates the possibility of deamination of Ara-C, and consequent elimination of its activity, by cytidine deaminase which converts the nucleoside Ara-C to Ara-uracil but is not active at the nucleotide level. (Camiener, G. W., Smith, C. G., Biochem. Pharmacol., 14, (1965) 1405.) Regarding Ara-C, see in general, Hsi, D., Wang, H., *Cancer Res.,* 33, (1973) 2816; Camiener, G. W., Smith, C. G., supra.; Camicner, G. W., *Biochem. Pharmacol.,* 16, (1967) 1681; Wechter, W. J., Johnson, M. A., Hall, C. M., Werner, D. T., Berger, A. E., Wenzel, A. H., Gish, D. T., Neil, G. L., *J. Med. Chem.,* 18, (1975) 339; Chou, T. C., Arlin, Z., Bayard, D. C., Philips, F. S., *Cancer Res.,* 37, (1977) 3561; Rustum, Y. M., Preisler, H. D., *Cancer Res.,* 39, (1979) 42; as well as Alberto, "Fundamentals in Cancer Chemotherapy," *Antibiotics Chemother.,* Vol. 23, pages 88–98 (Karger, Basel, 1978).

As can be seen, the Ara-C application of this invention represents an example of two categories of therapeutic drugs which can be employed, i.e., those wherein a phosphate group of the diphosphate linker is part of the therapeutic moiety per se (i.e., the metabolized Ara-CMP), and also those wherein phosphorylation occurs after the conventional therapeutic agent (Ara-C) has been administered. Other applicable drugs having a phosphate moiety as part of the chemical structure include cyclophosphamide, Diethylstilbesterol diphosphate, Polyestradiol phosphate, Estramustine phosphate, $NaPO_4$-$P^{32}$, chromic $PO_4$-$P^{32}$, radiopharmaceuticals, etc. Other drugs known to be phosphorylated metabolically include cytarabine, 6-mercaptopurine, Thioquanine, Acyclovir, etc. Exemplary drugs which, without unacceptably adverse effect, can retain a monophosphate group after cleavage of the diphosphate linkage of this invention (e.g., due to subsequent MP removal by phosphatase) include streptozocin and other alcohol-containing drugs where a phosphate may be cleaved by phosphate enzymes to the free alcohol. Likewise, any alcohol-containing drug can be phosphorylated and used with a DP or DP(A) linker.

Site selective phosphorylation on the therapeutic moiety A per se can be achieved using conventional chemical procedures. In general, the phosphorylation methods mentioned above will be applicable to the A compounds in conjunction with well known blocking and/or activation of the necessary portions of the molecule as described above in conjunction with the synthesis of linking arms. See, e.g., Amarnath, V., Broom, A. D. *Chem. Rev.* 1977, 77, 1983.

More generally, this invention will be applicable to essentially any therapeutic agent (or combinations of agents, e.g., known polymers having multiple (the same or different) pendant active agent molecules as discussed above)

which can be linked to the DP or DP(A) linker of this invention directly or by linker arm $L^1$. These agents will include especially anti-tumor agents such as Melphalan, Methotrexate, and other folate analogs, Daunomycin, Doxorubicin, Mitomycins, Bleomycins, Mitoxantrone, Dactinomycin, etc., but is not limited thereto. Other general classes and specific examples of therapeutic agents include toxins. Examples of toxins which may be employed are ricin, abrin, diphtheria toxin, Pseudomonas exotoxin A, ribosomal inactivating proteins, and mycotoxins, e.g., trichothecenes, such as verracarin. Trichothecenes are a species of mycotoxins produced by soil fungi of the class *fungi imperfecti* or isolated from *Baccharus megapotamica* (Bamburg, J. R., *Proc. Molec. Subcell Bio.* 8:41-110, 1983; Jarvis and Mazzola, *Acc. Chem. Res.* 15:338-395, 1982). Therapeutically effective modified toxins or fragments thereof, such as those produced through genetic engineering or protein engineering techniques, may be used. See, e.g., U.S. Pat. No. 4,744,981.

Of course, this invention will be especially applicable to targeting polypeptides which select activity sites which are especially effective in cleaving the DP and/or DP(A) bond. For DP, these will be sites containing effective amounts of phosphodiesterase I (EC 3.1.4.1) especially, but also 5'-nucleotidase (EC 3.1.3.5), acid phosphatase (EC 3.1.3.2), alkaline phosphatase [Sinkula, A. A., S. H. Yalkowsky, *J. Pharm. Sci,* 64 (1975) 189]. For DP(A), the sites will include those containing effective amounts of alkaline phosphatase or phosphoramidase (Sinkula et al., supra). Such sites will include tumors, but, in general, any cell will be applicable for targeting. The distribution of phosphtases and the other enzymes varies among the specificity and reaction rate, depending on location. H. N. Fernley, in "The Enzymes," 3rd ed., vol. 4, P. D. Boyer ,Ed., Academic, New York, N.Y., 1971. However, a major advantage of this invention is that phosphatase levels are greatly increased in tumors (F. Schapira, *Advan. Cancer Res.*, 18, 1973), especially in certain locations such as the liver. Phosphatases which are more predominant in the kidney, liver, and intestine will also be especially advantageous for clearance of immunoconjugates of radiolabeled ligands or chemotherapeutic drugs or metabolites thereof, since it is known that such compounds can undesirably accumulate in these areas.

Of course, this invention will also be applicable to target-specific delivery of a diagnostic moiety which need not be cleaved in situ, as well as to therapeutic agents which are able to exert their therapeutic effect without being cleaved.

Thus, in accordance with this invention, any desired diagnostic or therapeutic agent can be cleavably linked with an appropriate targeting group to optimize the desired effect on a locus in a patient, e.g., by appropriately matching an agent effective at a locus with a moiety able to target that locus, e.g., NR-Lu-10 Fab (breast tumors) conjugated to anti-breast cancer agents, e.g., diethylstilbesterol diphosphate, polyestradiol phosphate, estramustine phosphate, etc.

The conjugates of this invention will typically be administered for the same purposes as the therapeutic or diagnostic agent A is administrable. Thus, Ara-C targeted in accordance with this invention will be administrable for anti-tumor treatment analogously to the methods heretofore used to employ this leading chemotherapeutic agent in the treatment of cancer. Generally, suitable dosages will be in the same ranges conventionally known for the therapeutic or diagnostic agent A. In many instances, the dosage of agent A necessary may be reduced in view of the increased selectivity effected by this invention. Suitable dosages will vary according to such factors as the nature of the patient's illness, the number and location of target sites, any cross-reactivity of the targeting polypeptide with normal tissues, etc. A physician skilled in the field to which this invention pertains will be able to determine routinely the proper dosage of a particular conjugate of the present invention.

For example, for radionuclide chelates, administration will be, as is conventional, by injection, intravenously, intra-arterially, peritoneally, intratumorally, etc., depending on the particular site desired. Typically, from 0.001 to 50 mCi/kg of host will be used. For human hosts, the dosage will usually be about 10-50 mCi/70 kg of host, more usually about 25-35 mCi/70 kg of host. For lower mammals, e.g., mice, 1 mCi for biodistribution studies will be employed, while up to or greater than 500 mCi for imaging studies can be used. After administration of the diagnostic agent, e.g., radionuclide or paramagnetic metal, the host will be treated conventionally for detection or imaging. Where treatment is involved, similarly, subsequent procedure will be as is conventional.

The compounds of this invention can be administered in the usual galenic formulations and can be provided in the form of the usual kits. For example, a kit could comprise a container of A—$L^1$—DP(or DP(A))—$L^2$, wherein $L^2$ includes a protein conjugation group, as described above, and a container of the targeting polypeptide to be attached thereto. Thus, suitable pharmaceutically acceptable adjuvants will be all inorganic and organic compounds known for this purpose, e.g., including water, saline, buffers, antioxidizing agents (e.g., ascorbic acid), surfactants (e.g., lecithins, Tween®, Myrj®), etc., as long as these adjuvants do not have an adverse impact on the targeting polypeptide.

As can be seen from the wide variety of possible structures for the A moiety, a wide variety of conventional reactions will be applicable to formation of A—$L^1_n$—DP(or DP(A))—. When A is directly linked to DP, a phosphate group will normally be part of A and the chemistry described above will be applicable. When A is linked to DP via $L^1$, the chemistry to be employed in a given case will correspond to the A-linking moiety on $L^1$. Typically, the A-$L^1$ link will be via a conventional amide, ester, thioester, ether, thioether, etc., bond. Thus, the chemistry described above will be fully applicable. Fully analogous considerations apply to the DP(A) linker aspect of this invention.

The chemistry described above can be performed in essentially any order. For example, the various portions of the molecule can be prepared in any order as may be most convenient for a given application. Similarly, all or part of the chemistry can be performed before or after chelation of a given metal It is generally preferred to attach the targeting polypeptide as the last step to avoid interfering reactions with its functional group.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The entire text of all applications, patents and publications cited above and below are hereby incorporated by reference.

EXAMPLE 1

A ligand derivative (A), useful for chelation of a radionuclide and conjugation to a polypeptide, has the following formula:

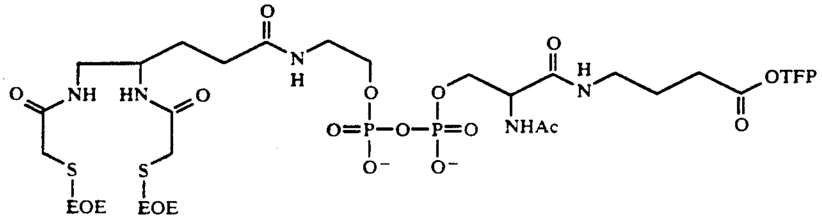

wherein

EOE is an ethoxyethyl sulfur protecting group, and COOTFP is a tetrafluorophenyl ester protein conjugation group.

In this compound, the linker arm $L^2$ is uncomplicated, as is the linker arm $L^1$, thus representing a particularly advantageous combination. This example illustrates the above-mentioned technique wherein the linker arm is made first, followed by condensation to the ligand so that the latter can be varied as desired, e.g., in experiments to improve labelling. Furthermore, the two linker arms, $L^1$ and $L^2$, are made independently whereby they can be worked on simultaneously. The final step in making the $L^1$—DP—$L^2$ complex is the phosphate coupling, followed by deprotection.

Ethanol amine phosphate, commercially available from Sigma, is protected with CBZ-Cl to form (1) using the conditions reported in Bodanszky, A., Bodanszky, M. "The Practice of Peptide Synthesis" Springer-Verlag (1984) New York, N Y. The blocked phosphate is activated for coupling by reaction with morpholine to yield (2) using the procedures reported in Moffatt et al., supra.

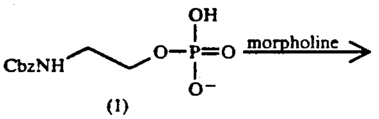

(1)

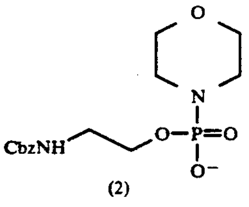

(2)

Synthesis of the remaining portion of the linker arm also begins with a commercially available starting material, viz., O-t-butyl serine (e.g., Bachem Chemicals). This compound is acetylated to form N-acetyl-O-t-butyl serine (3) by reacting 3.2 g of the mentioned starting compound with 360 μl of acetic anhydride at a temperature of 0° C. for 60 minutes. The N-acetylated product is then condensed with GABA benzyl ester at a temperature of 27° C. for 24 hours in order to produce 190 mg of the peptide (4). (GABA benzyl ester is synthesized by condensation of N-Boc-GABA with benzyl alcohol in the presence of dicyclohexylcarbodiimide (DCC) and dimethylaminopyridine (DMAP) at a temperature of 27° C. for 24 hours.) Treatment of the peptide product with TFA at a temperature of 27° C. for 120 minutes followed by reaction in situ with beta-cyanoethyl phosphate under conditions described in Brownfield et al, *Steroids*, 2, (1963) 597, yields the phosphorylated peptide (5). The cyanoethyl group is removed by conventional treatment with a base such as tri-n-butyl-amine to yield the free phosphate (5). Such a base minimizes cleavage of the ester. Compound (5) is then coupled with compound (2) to yield the protected linker arm (6). This reaction is conducted under the conditions described by Hong et al., e.g., 27° C. for 5 days in pyridine. Deprotection using $H_2$ and palladium on charcoal yields the desired amino acid (7). The latter is linked to the preferred radionuclide ligand NHS ester under conventional conditions, e.g., 27° C. for 120 minutes in THF or DMF. Preparation of the $N_2S_2$ ligand itself is described in EP 188,256 and U.S. patent application Ser. No. 07/065,017. Conversion of (8) to the TFP ester is by conventional water-soluble carbodiimide-based procedures using EDCI (Williams et al, supra.), e.g., by reaction of 8 with TFP at 27° C. for 24 hours.

Conjugation to the antibody and formation of the radionuclide chelate are carried out as described in the references cited above. In general, the radiolabeling reaction is conducted to form the radionuclide metal chelate prior to conjugation to the targeting polypeptide. Conventional procedures are used for the radiolabeling reaction. Suitable procedures include those presented in co-pending U.S. patent application Ser. No. 065,017.

For example, pertechnetate ($^{99m}TcO_4^-$ or perrhenate ($^{186}$ or $^{188}ReO_4^-$) are generally contacted with the chelating compound derivative in the presence of a reducing agent (e.g., a ferrous or stannous salt) to effect reduction of the radionuclide to an oxidation state at which chelation can occur. Alternatively, the pertechnetate or perrhenate may be reduced in the presence of a relatively labile exchange agent such as gluconic acid or citric acid to form intermediate complexes ($^{99m}$Tc-gluconate or $^{188}$Re-citrate). When the intermediate complexes are contacted with the chelating compound under appropriate reaction conditions (which may involve heating), the radionuclide metal is transferred to the chelating compound in the exchange reaction, thereby producing a stable radionuclide metal chelate.

Chelates of $^{212}Pb$, $^{212}Bi$, and $^{109}Pd$ may be prepared by combining the appropriate salt of the radionuclide with the chelating compound and incubating the reaction mixture at room temperature or at higher temperatures. It is not necessary to treat the lead, bismuth, palladium, and copper radioisotopes with a reducing agent prior to chelation, as such isotopes are already in an oxidation state suitable for chelation.

The resulting radiolabeled molecule is combined with the desired targeting polypeptide in a buffered aqueous solution under conditions that do not denature or otherwise adversely affect the desired biological activity of the targeting polypeptide. For example, the reaction may be conducted at a temperature of about 20°-37° C. and at a pH of about 9-11. The 2,3,5,6-tetrafluorophenyl ester on the radiolabeled compound reacts with epsilon amine groups on lysine residues of the targeting polypeptide, thereby forming amide bonds.

The synthetic scheme is summarized below:

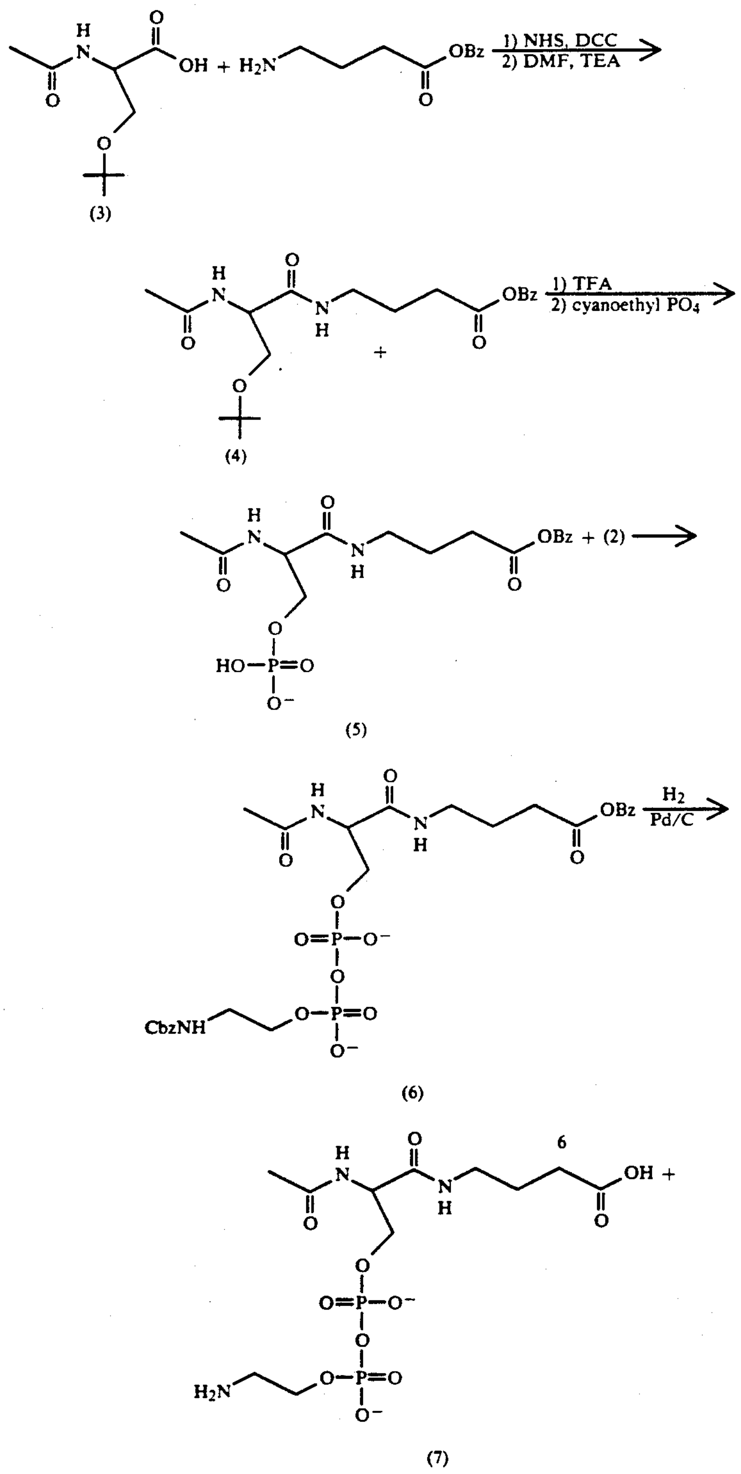

(3)

(4)

(5)

(6)

(7)

-continued

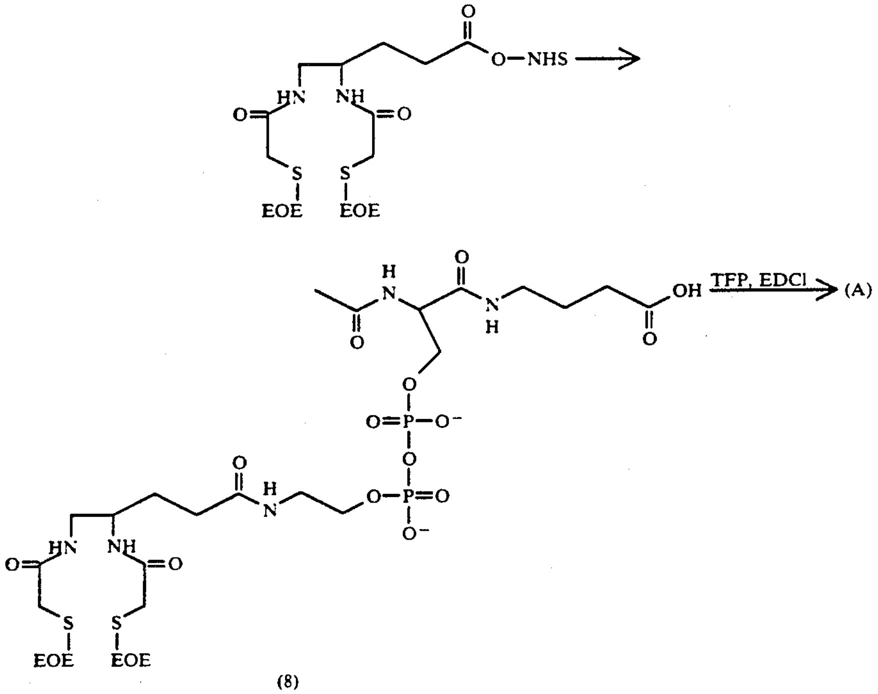

(8)

EXAMPLE 2

An alternative method is utilized to prepare the same ligand derivative of Example 1. Analogously to Example 1, the n-acetyl-O-benzyl ether of serine is prepared from the commercially available 0-benzyl ether of serine (Adams Chemical Company, Rockville, Ill.). The GABA-t-butyl ester is prepared analogously to Compound (4) above. The two compounds are then condensed analogously to the similar condensation performed in Example 1. After conventional cleavage of the benzyl protecting group using conditions described in the references cited above, the resultant primary hydroxyl group is reacted with dibenzylphosphorochloridate under conditions described in Kenner et al, supra. The benzyl protecting groups on the resultant product are then conventionally cleaved to yield the desired free phosphate (having the structure of (5) but with 0-t-Bu in place of o-Bz). Separately, instead of CBZ-protected ethanolamine phosphomorpholidate, the analogous N-Boc protected compound is prepared analogously to the steps recited in Example 1. Reaction of the N-Boc protected ethanol amine phosphomorpholidate with the t-Bu analog of (5) yields the N-Boc-t-butyl ester derivative of (6). Conventional cleavage of the remaining protecting groups carried out in accordance with the well known procedures described above, yields (7). The remaining procedures for attaching the ligand, radiolabeling, and attaching the targeting polypeptide are as described in Example 1. Alternatively, a different ligand comprising a spacer that terminates in an active ester may be substituted for the $N_2S_2$ ligand.

EXAMPLE 3

Using the procedures of Examples 1 and/or 2, Compound (5) or the t-butyl ester analog thereof is prepared. Ara-CMP morpholidate (9) is prepared in accordance with the conventional procedures described above, e.g., those described by Moffatt et al, from commercially available Ara-CMP and morpholine. Ara-C MP morpholidate is coupled to (5) to yield (10) also using conditions reported by Moffatt et al. Conventional removal of the benzyl blocking group by treatment with hydrogen and palladium on charcoal, followed by conventional conversion to the TFP ester as described in Example 1 via EDCI coupling, yields the desired compound (11). The latter is then conventionally conjugated with any desired protein, such as a tumor-specific monoclonal antibody, using the conventional procedures mentioned above. The synthetic sequence is shown schematically below:

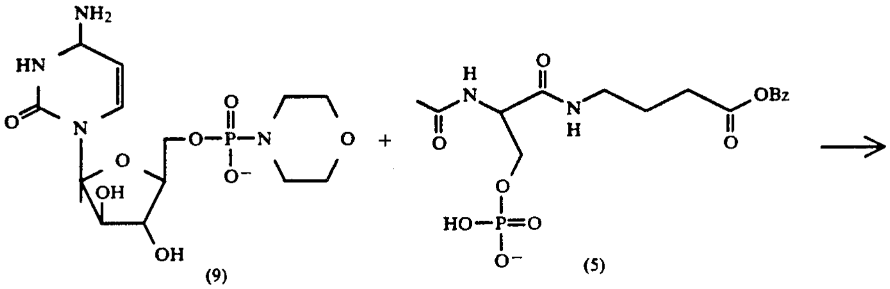

(9) (5)

-continued

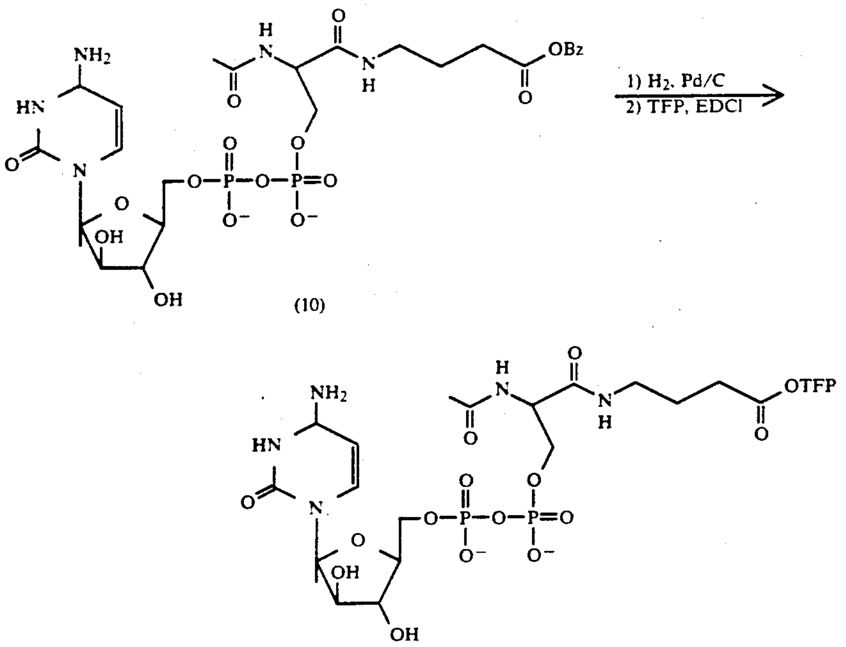

(10)

EXAMPLE 4

Verracarin A (VA) (U.S. Pat. No. 4,744,981) contains an OH group which can be used to diphosphate link it to a polypeptide. The secondary hydroxyl of VA is phosphorylated (12) for use in forming a diphosphate linker. (Bis)-trichloroethyl-phosphochloridate is used especially since applicable subsequent deprotection techniques to produce the free phosphate, e.g., with Zn/Cu couple/DMF, do not harm the macrocycle. (Srinivasan, A; Amarnath, V.; Broom, A. D.; Zou, F. C.; Cheng, Y.-C. J. Med. Chem., 27 1710 (1984)).

Using the methods of Examples 1 and 2, the phosphate linker (5) is prepared.

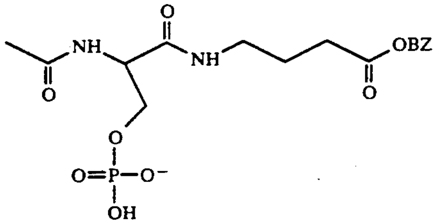

(5) is then reacted with morpholine as described in Examples 1 and 2 and hydrogenated to remove the benzyl ester, also using the procedures of the foregoing examples. The phosphorylated VA derivative (12) is then reacted with the activated morpholinated phosphate linker (13) under the conditions of Examples 1 and 2 (NHS=N-hydroxysuccinimide) to produce the corresponding VA diphosphate linker derivative. This free acid is conjugated to antibody either via direct coupling or by first making an active ester, as discussed above. This chemistry is summarized in the following scheme.

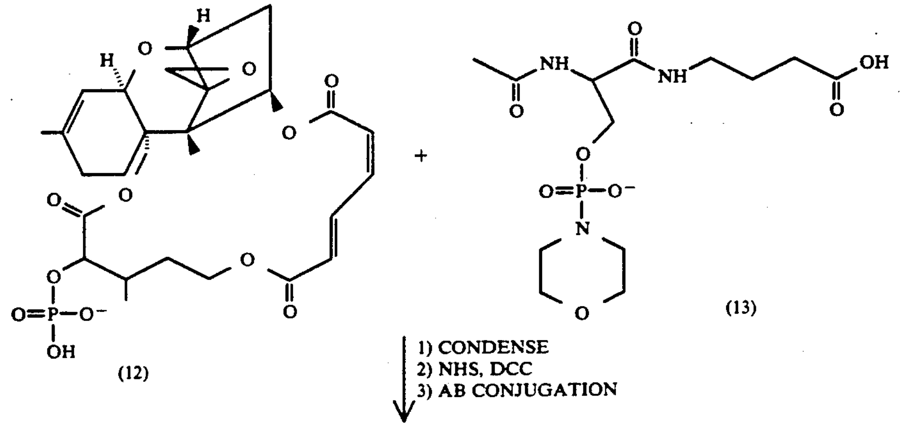

(12) (13)

-continued

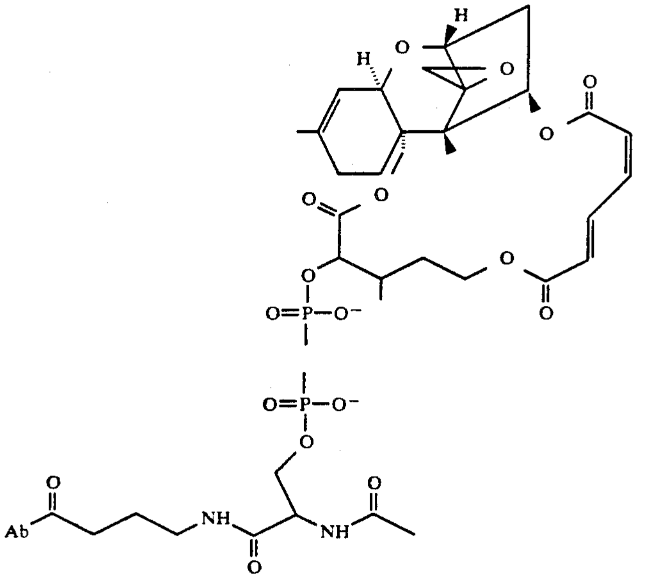

EXAMPLE 5

The alcohols of a dextran are phosphorylated using the techniques described in Examples 1-4 to form a multiphosphorylated derivative of dextran. Dextran is reacted with a single equivalent of morpholinophosphate linker as described in Example 4. This is followed by removal of the carboxylate protecting group to prove an arm for antibody conjugation. Next, an excess of morpholinophosphorylated drug such as Ara-C described in Exaple 3 is added top form a diphosphate linked drug moiety with all other available phosphates on the dextran. Under the influence of the enzymes described above, the dextran complex is released via the diphosphate linker to the antibody and active phosphorylated drug is released via the diphosphate linkers to the dextran. This chemistry is depicted in Scheme 1.

Scheme 1

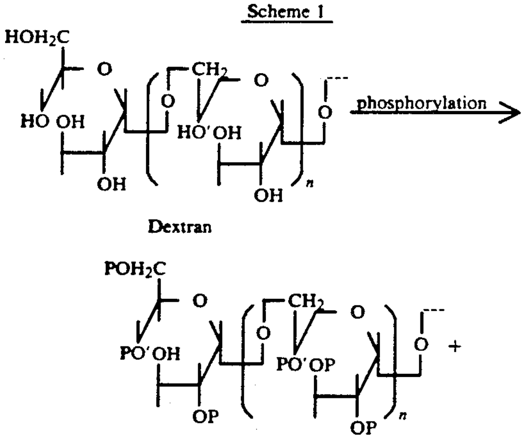

P = phosphate

-continued
Scheme 1

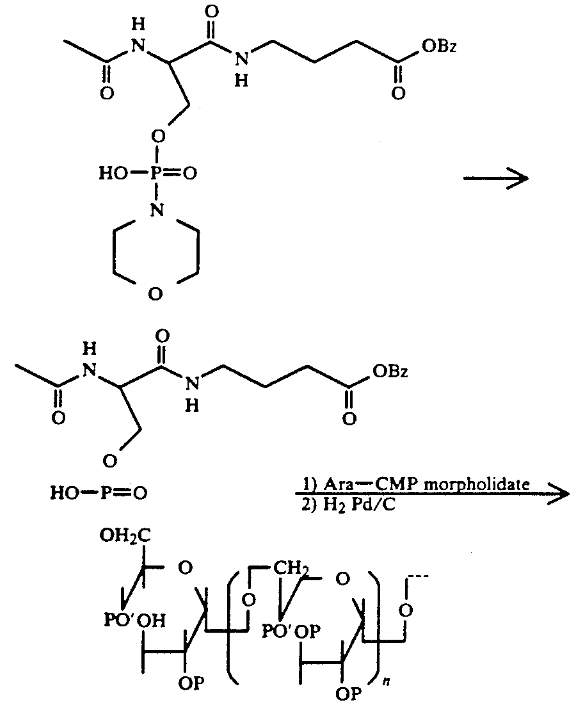

-continued
Scheme 1

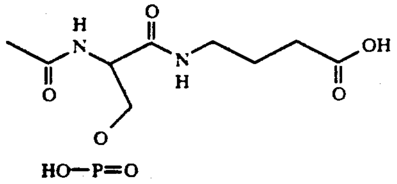

Scheme 2

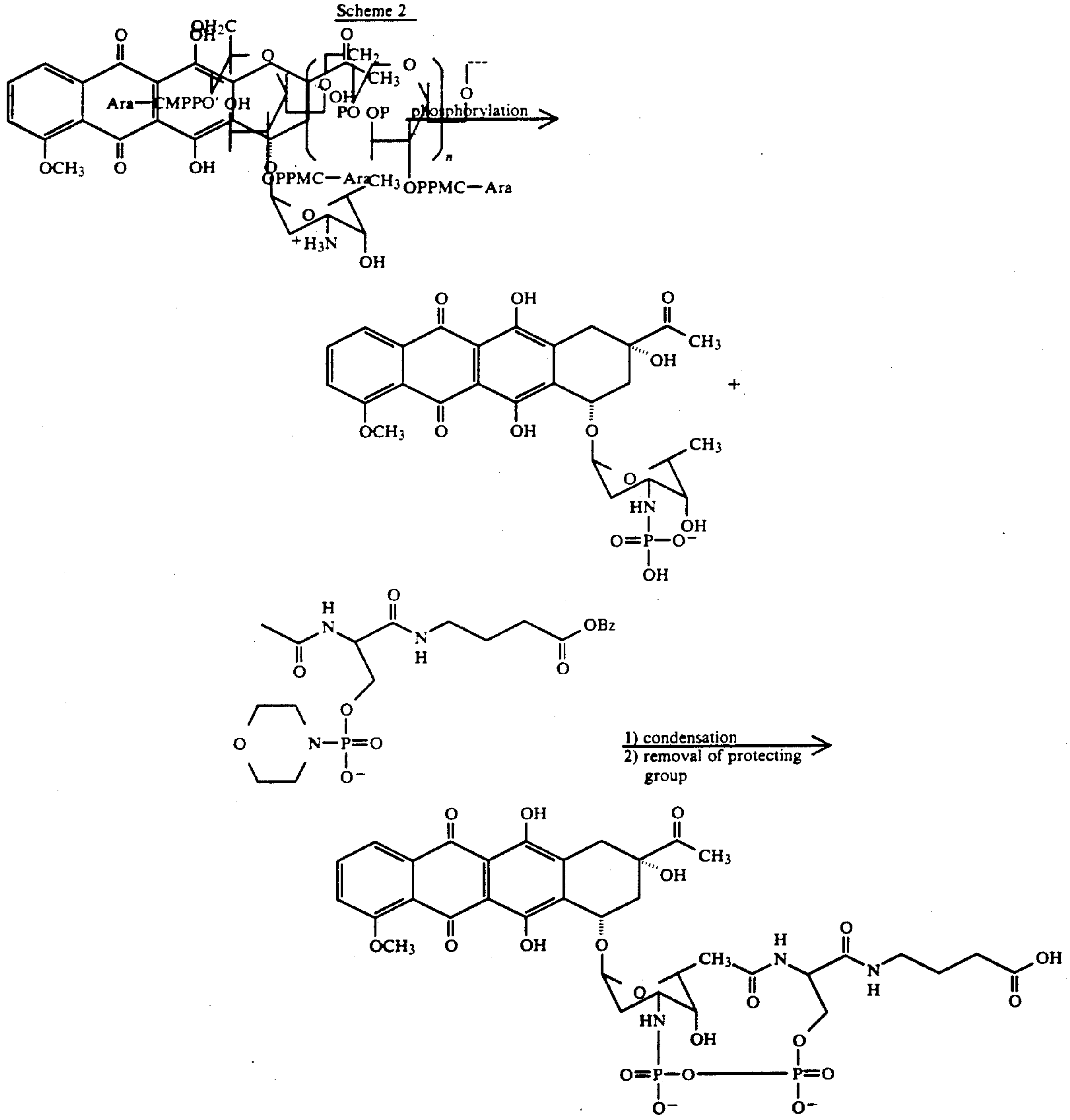

EXAMPLE 6

Daunomycin is phosphorylated under the reactions of Examples 1-4. The phosphorylated derivative is then reacted with the morpholinated phosphate linker (13) of Example 4 to form a phosphoramide linked daunomycin molecule ready for conjugation to, e.g., an antibody as described above.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

I claim:

1. A conjugate, useful for targeting of an active agent to a desired site, comprising an active agent cleavably linked to a moiety effective for targeting to said site, of the formula $$A—L^1_n—DP—L^2—\text{polypeptide}$$

wherein

DP is diphosphate, $L^1$ is a bridging spacer group, n is 0 or 1,

A is an active agent or a portion thereof

"polypeptide" is effective for targeting A to a desired site, and $L^2$ is an oligopeptide linking arm.

2. A conjugate of claim 1, wherein the amino acid monomer of the oligopeptide $L^2$ which is linked to DP is serine or threonine.

3. A conjugate of claim 2, wherein $L^2$ is —Ser—GABA— or a derivative thereof.

4. A conjugate, useful for targeting of an active agent to a desired site, comprising an active agent cleavably linked to a moiety effective for targeting to said site, of the formula $$A—L^1_n—DP—L^2—\text{polypeptide}$$

wherein

DP is diphosphate, n is 1, $L^1$ is a bridging spacer group containing about 2-10 atoms, A is an active agent or a portion thereof, and "polypeptide" is effective for targeting A to a desired site.

5. A conjugate of claim 4, wherein $L^1$ contains at least one peptide bond.

6. A conjugate, useful for targeting of an active agent to a desired site, comprising an active agent cleavably linked to a moiety effective for targeting to said site, of the formula $$A—L^1_n—DP(A)—L^2—\text{polypeptide}$$

wherein

DP(A) is amidated diphosphate, $L^1_n$ is a bridging spacer group, n is 0 or 1, $L^2$ is a linking arm, A is an active agent or a portion thereof, and "polypeptide" is effective for targeting A to a desired site.

7. A conjugate of claim 6, wherein A is a radionuclide metal chelate or an anti-tumor agent.

8. A conjugate comprising at least two groups ($A—L^1_n—DP—L^2—$) as defined in claim 1 bonded to a pharmacologically acceptable carrier polymer which is bonded to a targeting moiety.

9. A conjugate comprising at least two groups ($A—L^1_n—DP(A)—L^2—$) as defined in claim 6 a pharmacologically acceptable carrier polymer which is bonded to a targeting moiety.

10. A conjugate of claim 8, wherein said polymer is dextran.

11. A conjugate of claim 1, wherein the polypeptide is a polyclonal or monoclonal antibody.

12. A conjugate of claim 4, wherein the polypeptide is a polyclonal or monoclonal antibody.

13. A conjugate of claim 6, wherein the polypeptide is a polyclonal or monoclonal antibody.

14. A conjugate of claim 11, wherein n is O and A or a monophosphorylated metabolite thereof is pharmacologically therapeutic.

15. A conjugate of claim 11, wherein n is O, A is Ara-C and the polypeptide is a monoclonal antibody of an immunospecific fragment thereof.

16. A conjugate of claim 11, wherein A is an antitumor agent or a radionuclide metal chelate.

17. A conjugate of claim 4, wherein A is an antitumor agent or a radionuclide metal chelate.

18. A pharmaceutical composition comprising a diagnostically or therapeutically effective amount of conjugate of claim 1 and a pharmaceutically acceptable carrier.

19. A pharmaceutical composition comprising a diagnostically or therapeutically effective amount of conjugate of claim 9 and a pharmaceutically acceptable carrier.

20. A pharmaceutical composition comprising a diagnostically or therapeutically effective amount of conjugate of claim 6 and a pharmaceutically acceptable carrier.

21. A pharmaceutical composition comprising a diagnostically or therapeutically effective amount of conjugate of claim 8 and a pharmaceutically acceptable carrier.

22. A pharmaceutical composition comprising a diagnostically or therapeutically effective amount of conjugate of claim 9 and a pharmaceutically acceptable carrier.

23. A method of targeting a pharmaceutical agent to a desired site in a patient or sample comprising administering to the patient or contacting the sample with a conjugate of claim 1.

24. A method of targeting a pharmaceutical agent to a desired site in a patient or sample comprising administering to the patient or contacting the sample with a conjugate of claim 6.

25. A method of targeting a pharmaceutical agent to a desired site in a patient or sample comprising administering to the patient or contacting the sample with a conjugate of claim 4.

26. A method of targeting a pharmaceutical agent to a desired site in a patient or sample comprising administering to the patient or contacting the sample with a conjugate of claim 8.

27. A method of targeting a pharmaceutical agent to a desired site in a patient or sample comprising administering to the patient or contacting the sample with a conjugate of claim 9.

* * * * *

65

UNITED STATES PATENT AND TRADEMARK OFFICE

CERTIFICATE OF CORRECTION

PATENT NO. : 5,094,848

DATED : March 10, 1992

INVENTOR(S) : Brixner

It is certified that error appears in the above-identified patent and that said Letters Patent is hereby corrected as shown below:

In column 32, line 27 [claim 19], please delete "9" and insert --4-- therefor.

In column 32, line 15 [claim 15], please delete "of" and insert --or-- therefor.

Signed and Sealed this

Twenty-first Day of November, 1995

Attest:

Bruce Lehman

BRUCE LEHMAN

Attesting Officer

Commissioner of Patents and Trademarks